United States Patent
Massaro

(10) Patent No.: US 7,438,857 B2
(45) Date of Patent: Oct. 21, 2008

(54) LIQUID HANDLING TOOL HAVING POROUS PLUNGER

(75) Inventor: Peter Massaro, Burlington, CT (US)

(73) Assignee: Protedyne Corporation, Windsor, CT (US)

( * ) Notice: Subject to any disclaimer, the term of this patent is extended or adjusted under 35 U.S.C. 154(b) by 766 days.

(21) Appl. No.: 10/622,414

(22) Filed: Jul. 18, 2003

(65) Prior Publication Data

US 2004/0018119 A1    Jan. 29, 2004

Related U.S. Application Data

(60) Provisional application No. 60/397,989, filed on Jul. 23, 2002.

(51) Int. Cl.
B01L 3/02 (2006.01)
(52) U.S. Cl. .................. 422/100; 422/63; 422/64; 422/65; 422/99; 436/180; 73/864.13; 222/309
(58) Field of Classification Search ............ 422/62–65, 422/99–101; 436/180; 73/864.13; 222/309
See application file for complete search history.

(56) References Cited

U.S. PATENT DOCUMENTS

| | | | |
|---|---|---|---|
| 3,290,946 A | 12/1966 | Pursell | |
| 3,572,552 A | 3/1971 | Guinn | |
| 3,656,351 A | 4/1972 | Raczak | |
| 3,760,639 A | 9/1973 | Sokol et al. | |
| 3,855,868 A | 12/1974 | Sudvaniemi | |
| 3,945,254 A | 3/1976 | Rebold | |
| 3,954,014 A | 5/1976 | Andrews, Jr. et al. | |
| 3,991,617 A | 11/1976 | d'Autry | |
| 4,037,464 A | 7/1977 | Wenander | |
| 4,052,161 A | 10/1977 | Atwood et al. | |
| 4,099,548 A | 7/1978 | Sturm et al. | |
| 4,237,095 A | 12/1980 | Suovaniemi et al. | |
| 4,294,125 A | 10/1981 | Lee | |
| 4,304,138 A | 12/1981 | Tervamaki | |
| 4,555,957 A | 12/1985 | Frankel et al. | |
| 4,567,780 A | 2/1986 | Oppenlander et al. | |
| RE32,210 E | 7/1986 | d'Autry | |
| 4,599,220 A | 7/1986 | Yonkers et al. | |
| 4,801,434 A | 1/1989 | Kido et al. | |
| 4,810,348 A | 3/1989 | Sarrine et al. | |
| 5,055,263 A | 10/1991 | Meltzer | |
| 5,193,403 A | 3/1993 | Burgisser | |

(Continued)

FOREIGN PATENT DOCUMENTS

FR    2801108 A1    5/2001

(Continued)

*Primary Examiner*—Jill Warden
*Assistant Examiner*—Jyoti Nagpaul
(74) *Attorney, Agent, or Firm*—Wolf, Greenfield & Sacks, P.C.

(57) ABSTRACT

A robotically manipulable sample handling tool, such as a colony picking head or robotic pipetting tool, includes needles arranged on the tool. Actuators are associated with each needle to control flow for the needle. A plurality of plungers are each associated with a needle, and movement of the plungers can actuate a corresponding needle. Each of the plungers has a passageway that may be opened or closed, e.g., to move the corresponding needle and/or draw fluid into/expel fluid from the needle when the plunger is moved in the tool body. The actuators are arranged so that plunger passageways may be individually controlled by a controller.

15 Claims, 5 Drawing Sheets

U.S. PATENT DOCUMENTS

| | | | |
|---|---|---|---|
| 5,347,878 A | 9/1994 | Suovaniemi | |
| 5,370,843 A | 12/1994 | Chiodo | |
| 5,381,699 A | 1/1995 | Dansereau et al. | |
| 5,413,006 A | 5/1995 | D'Autry | |
| 5,465,629 A | 11/1995 | Waylett, Jr. | |
| 5,505,097 A | 4/1996 | Suovaniemi et al. | |
| 5,525,302 A | 6/1996 | Astle | |
| 5,614,153 A | 3/1997 | Homberg | |
| 5,670,113 A | 9/1997 | Akong et al. | |
| 5,700,959 A | 12/1997 | Homberg | |
| 5,736,105 A * | 4/1998 | Astle | 422/100 |
| 5,770,159 A | 6/1998 | d'Autry | |
| 5,792,424 A | 8/1998 | Homberg et al. | |
| 5,964,381 A | 10/1999 | El-Hage et al. | |
| 5,983,733 A | 11/1999 | Strandberg et al. | |
| 6,019,004 A | 2/2000 | Conley et al. | |
| 6,033,911 A * | 3/2000 | Schultz et al. | 436/49 |
| 6,123,905 A | 9/2000 | Torti et al. | |
| 6,168,761 B1 | 1/2001 | Kelly et al. | |
| 6,171,553 B1 | 1/2001 | Petrek | |
| 6,197,259 B1 | 3/2001 | Kelly et al. | |
| 6,199,435 B1 | 3/2001 | Wilmer et al. | |
| 6,235,002 B1 | 5/2001 | Carver, Jr. et al. | |
| 6,244,119 B1 | 6/2001 | Theran | |
| 6,248,295 B1 | 6/2001 | Petrek | |
| 6,258,324 B1 | 7/2001 | Yiu | |
| 6,365,110 B1 | 4/2002 | Rainin et al. | |
| 6,372,183 B1 | 4/2002 | Akong et al. | |
| 6,372,185 B1 | 4/2002 | Shumate et al. | |

FOREIGN PATENT DOCUMENTS

| | | | |
|---|---|---|---|
| WO | WO9116976 A1 | 11/1991 | |
| WO | WO9213638 A1 | 8/1992 | |
| WO | WO9313423 A1 | 7/1993 | |
| WO | WO9325914 A1 | 12/1993 | |
| WO | WO9703752 A2 | 2/1997 | |
| WO | WO9810265 A1 | 3/1998 | |
| WO | WO9820973 A2 | 5/1998 | |
| WO | WO9831465 A1 | 7/1998 | |
| WO | WO9932870 A1 | 7/1999 | |
| WO | WO0013609 A2 | 3/2000 | |
| WO | WO0023782 A2 | 4/2000 | |

* cited by examiner

LIQUID HANDLING TOOL HAVING POROUS PLUNGER

RELATED APPLICATIONS

This application claims priority to U.S. provisional application Ser. No. 60/397,989, filed Jul. 23, 2002.

BACKGROUND OF THE INVENTION

1. Field of Invention

This invention relates to sample handling tools, such as robotically manipulated pipetting devices.

2. Related Art

Robotically manipulated tools having a plurality of sample handling needles are widely used, for example, in proteomic and genomic research. These devices are used to move material samples both to and from a variety of different work areas, such as microtiter trays, gels having separated DNA fragments, and other material holding devices. Some such tools may have a plurality of needles arranged in an array that corresponds to wells in a microtiter tray, such as the commonly-known 96-well or 384-well plate. The array of needles arranged to correspond with all of the wells in a microtiter tray may allow material to be simultaneously deposited in, and removed from, wells in the microtiter tray, thus increasing the speed at which a plurality of samples in a microtiter tray may be processed.

SUMMARY OF THE INVENTION

In one illustrative embodiment in accordance with the invention, a robotically manipulable material handling tool includes a tool body and a plurality of needles mounted to the tool body. Each of the plurality of needles is constructed and arranged to remove material from a work area and deposit material on a work area. The tool also includes a plurality of plungers with each of the plurality of plungers associated with a corresponding one of the plurality of needles. The plungers may be movable in a channel to create suction/pressure that causes the corresponding needle to be actuated. The plungers may be porous, e.g., have a hole, channel or other passageway that allows fluid (i.e., gas or liquid) to pass through the plunger. In some embodiments, the passageway in the plunger may be controllably opened or closed so that the plunger and associated needle may be controlled to aspirate or dispense liquid or not. For example, if the passageway is closed, movement of the plunger in an associated channel (e.g., cylindrical bore) may create a suction at the needle and cause the needle to aspirate a liquid. In contrast, if the passageway is opened, movement of the plunger may not create a suction at the needle since air or other fluid may pass through the passageway.

In another illustrative embodiment, passageways in plungers may be individually addressed, e.g., opened or closed, so that each of the needles may be individually controlled to pick up and/or dispense samples. For example, a plurality of plungers may be all mounted to a common drive mechanism that moves all of the plungers relative to a channel block. For plungers that have their passageway closed, the plunger may create suction/pressure to actuate its corresponding needle as the plungers move. However, for plungers that have their passageway open, the plunger may not create suction/pressure to actuate its corresponding needle. As a result, if passageways in individual plungers can be individually addressed, individual needles can be actuated while other needles may be inactive.

In another aspect of the invention, individual passageways in plungers may be addressed using a matrix of membrane valves. The valves and associated control devices may be arranged to minimize the number of control signals needed to individually address plungers/needles.

These and other aspects of the invention will be apparent and/or obvious from the following description of illustrative embodiments and the appended claims.

BRIEF DESCRIPTION OF THE DRAWINGS

Illustrative embodiments in accordance with the invention are described below with reference to the following drawings, in which like numerals reference like elements, and wherein.

DETAILED DESCRIPTION

Various aspects of the invention are described below with reference to illustrative embodiments. However, it should be understood that the invention is not limited to those embodiments described below, but instead may be used in any suitable system or arrangement.

In one aspect of the invention, plungers in a sample handling tool may have a passageway that can be selectively opened or closed. Selective opening or closing of the passageway may allow a needle associated with each plunger to be selectively actuated. Such actuation may include moving a needle relative to the tool, such as extending the needle away from the tool apart from other needles on the body, controlling flow in the needle, such as drawing fluid into or expelling fluid out from the needle, or otherwise causing the needle to perform one or more material handling functions. In addition, the tool controller may simultaneously actuate all needles in the array, or simultaneously actuate selected groups of needles, such as all or selected needles in a particular row or column of needles. This arrangement may allow individual control of needles without requiring a controller to output an individual control signal for each needle.

Figure 1:
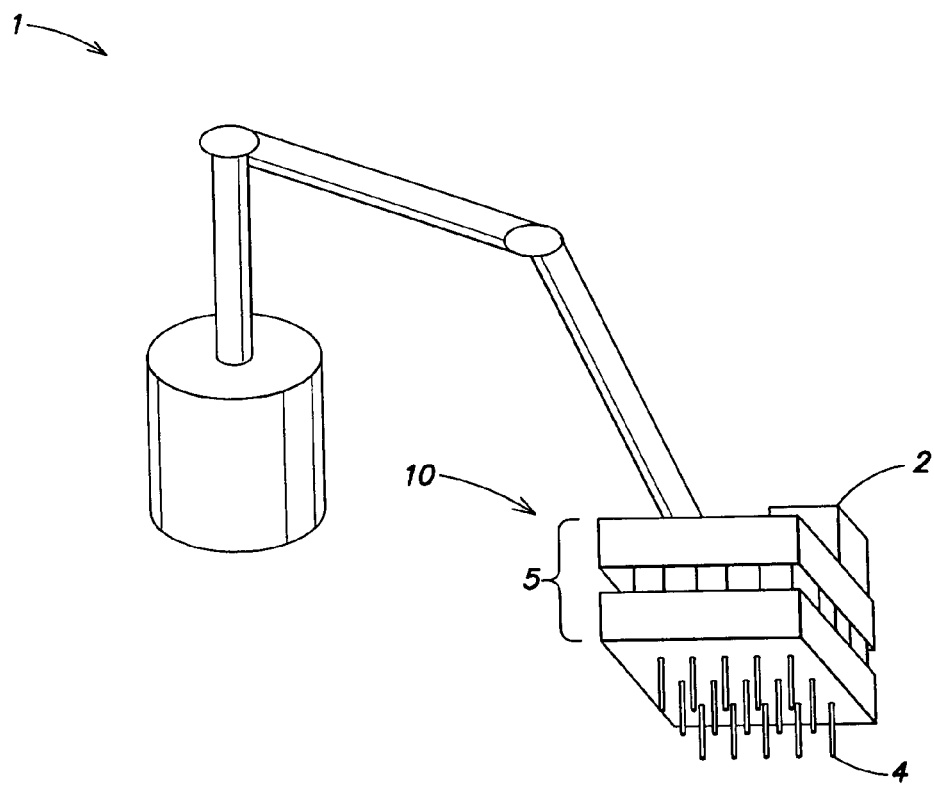
FIG. 1 is a schematic diagram of a robotically manipulated tool in accordance with the invention.

FIG. 1 is a schematic diagram of a robot 1 manipulating a material handling tool 10 in accordance with the invention. The robot 1 may move the material handling tool 10 and allow needles 4 on the tool 10 to pick up and/or deposit material on one or more work areas, such as microtiter trays, gels containing separated DNA fragments or other biologic materials, etc. For example, the robot 1 may move the tool 10 so that one or more needles 4 are appropriately positioned with respect to a microtiter tray and then actuate one or more needles 4 to remove material from, or deposit material in, wells in the microtiter tray. Those of skill in the art will understand that the needles may be actuated to perform other material handling operations, such as colony or plaque picking at the direction of a machine vision system. The purposes and methods for such material handling are well known to those in the art and not described in detail herein.

Although the robot 1 is shown in FIG. 1 as having a base and an articulated arm, the robot 1 may be of any suitable type or construction and may be capable of moving the tool 10 in any suitable number of degrees of freedom. For example, the robot may be a gantry-type robot capable of moving the tool 10 in three degrees of freedom. Of course, other suitable robotic configurations capable of moving the tool 10 in one or more degrees of freedom may be used. The tool 10 and robot 1 may include a coupling to allow the robot 1 to exchange the tool 10 for other tools, thereby allowing the robot 1 to perform automated operations with different tools. The robot 1 or system controller may include a vision system or other suitable device to control positioning of needles 4 with respect to target areas, as is well known. In addition, a connection, e.g., quick disconnect coupling, between the tool 10 and the robot 1 may provide physical support to the tool 10 as well as provide electrical power, control signals, a fluid supply or other fluid signal, etc. As used herein, "fluid" refers to gases and/or liquids.

In the illustrative embodiment of FIG. 1, the tool 10 includes a controller 2 that outputs signals to actuators in the controller that cause corresponding needles 4 to be actuated. As discussed above, actuation of a needle 4 may cause the needle 4 to move relative to the tool 10, such as extend away from the tool to pick or place material on a work area, control flow in the needle, such as drawing fluid into or expelling fluid out from the needle, or otherwise cause the needle to perform one or more material handling functions. In this illustrative embodiment, the controller 2 and needles 4 are all mounted to a body 5 of the tool 10, but portions of the controller 2 may be located off the tool 10. Although in this illustrative embodiment the body 5 has a box-like shape, the body 5 may be arranged in any suitable way. Further, the needles 4 in this illustrative embodiment are arranged in a 5×4 array and extend from a bottom of the body 5, but any suitable number of needles 4 may be arranged in any suitable way on the body 5, e.g., to accommodate particular well patterns in a microtiter tray. The needles 4 may be arranged to receive removable pipette tips or other devices to handle materials, or may be arranged to handle materials directly.

The controller 2, which may in some embodiments be provided off of the tool 10, may provide any suitable signal or combination of signals to the actuators to actuate the needles 4. For example, the controller 2 may provide electrical signals, magnetic signals, optical signals, fluid signals (e.g., changes in fluid pressure and/or flow), or combinations of such signals, such as providing both an electrical signal and a fluid signal to the actuators. Typically, signals provided by the controller 2 will depend upon the type of actuators. For example, the actuators may be pneumatically-controlled fluid valves that open, close or otherwise change state based on a fluid signal. Of course, the actuators may include electrically-controlled fluid valves, relays, or other suitable devices to actuate a corresponding needle. For example, the tool 10 may include one actuator for each needle, where each actuator includes a valve and associated pneumatic ram such that when the valve is open and air pressure is supplied through the open valve, the pneumatic ram may extend, and thereby extend a corresponding needle 4 from the body 5. Thus, the actuators may be responsive to two signals received from the controller 2 to actuate the needles 4. Having the actuators respond to two signals from the controller 2 may allow for matrix-type addressing of the actuators, as discussed in more detail below.

The controller 2 may operate autonomously to actuate the needles 4 or operate at the direction of a higher level controller that is part of a material handling system. For example, the controller 2 may receive a signal to activate a particular needle or group of needles at a particular time and/or position of the tool 10, and generate and output appropriate signals to cause the desired actuation. The controller 2 may receive the signals in any suitable way, such as by wired and/or wireless link, and in any suitable format and/or communications protocol. The controller 2 and/or higher level controller may include any suitable general purpose data processing system, which can be, or include, a suitably programmed general purpose computer, or network of general purpose computers, and other associated devices, including communication devices, and/or other circuitry or components necessary to perform the desired input/output or other functions. The controllers can also be implemented at least in part as single special purpose integrated circuits (e.g., ASICs), or an array of ASICs, each having a main or central processor section for overall, system-level control and separate sections dedicated to performing various different specific computations, functions and other processes under the control of the central processor section. The controllers can also be implemented using a plurality of separate dedicated programmable integrated or other electronic circuits or devices, e.g., hardwired electronic or logic circuits, such as discrete element circuits or programmable logic devices. The controllers may also include other devices, such as an information display device, user input devices, such as a keyboard, user pointing device, touch screen or other user interface, data storage devices, communication devices or other electronic circuitry or components.

Figure 2:
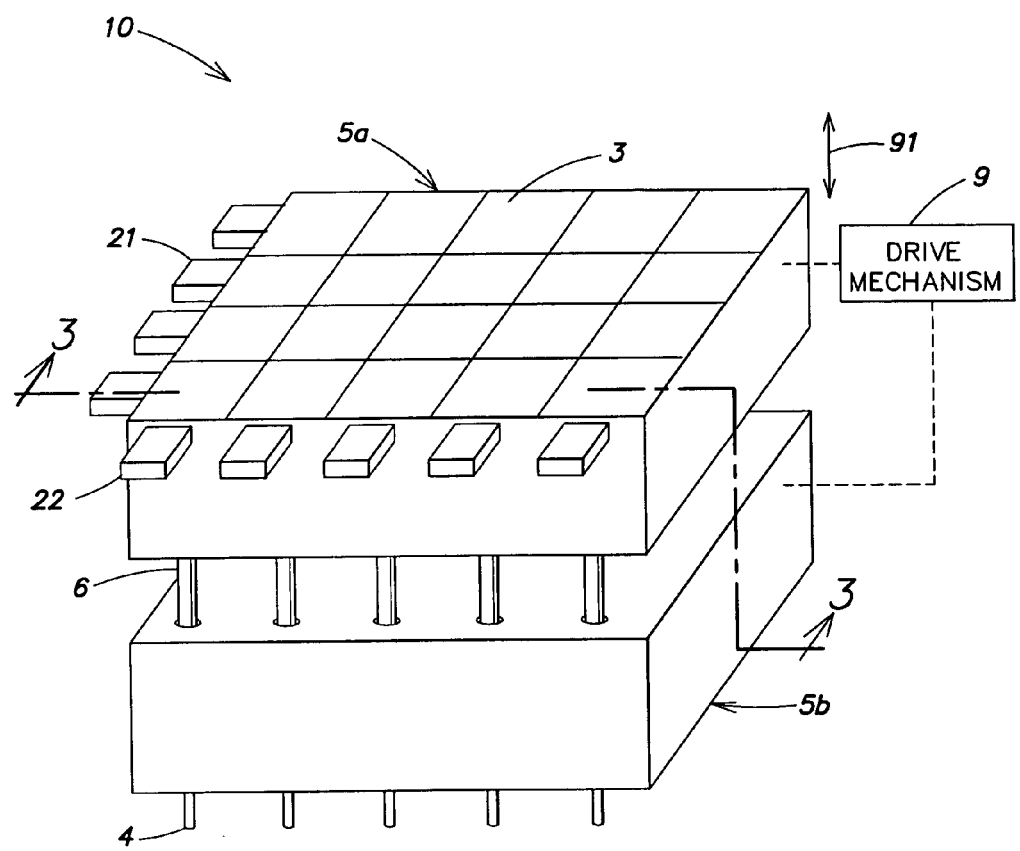
FIG. 2 is a schematic, perspective view of a tool in accordance with the invention.

FIG. 2 shows a perspective view of a tool 10 in accordance with the invention. In this illustrative embodiment, the controller 2 includes a 5×4 array of actuators 3 that are each associated with a corresponding needle 4. Thus, when an actuator 3 receives appropriate signals, the corresponding needle 4 may be actuated, e.g., fluid flow in the needle may be controlled and/or the needle 4 may be moved relative to the body 5. In this illustrative embodiment, the controller 2 includes four control switches 21 that are associated with actuators 3 in rows across the tool 10, and drive switches 22 that are associated with actuators 3 in columns on the tool 10. Control signals may be provided to the control switches 21 and drive switches 22 by a portion of the controller 2 (e.g., a data processor and associated memory) on the tool 10, or by another source off of the tool 10. Based on these control signals, the control switches 21 and drive switches 22 may provide suitable signals to the actuators 3 to actuate a particular needle or needles. The switches 21 and 22 may be any suitable device capable of responding to a control signal and providing a signal to corresponding actuators 3. For example, the switches 21 and 22 may include electrically-controlled valves capable of switching an associated line between one or more fluid lines, e.g., sources of relatively high or low pressure, or sources of fluid flow. Pressure or other fluid flow sources may be provided to the switches 21 and 22 by lines (not shown) that lead to a pump, metering piston, reservoir or other devices off of the tool body 10.

It should be understood that although the actuators 3 in this illustrative embodiment are arranged in columns and rows, the actuators 3 may be logically grouped in any suitable way and in any suitable pattern. Further, the tool 10 is not limited to a 5×4 array, but instead may have any suitable number of actuators and/or needles arranged in any suitable pattern, such as a pattern that allows the needles 4 to interact with standard 96-well, 384-well or other size/configuration microtiter trays or other material sample holders. Thus, the 5×4 array in this illustrative embodiment is used for simplicity and ease of reference, but should in no way be interpreted as limiting aspects of the invention in any way.

In this illustrative embodiment, the tool 10 also includes a drive mechanism 9 that is capable of moving an upper portion 5a of the body 5 relative to the lower portion 5b, e.g., in a direction shown by the arrow 91. Such movement may cause plungers 6 secured to the upper portion 5a to move relative to the lower portion 5b and create suction/pressure for each of the needles 4 to aspirate/dispense a sample. The drive mechanism 9 may take any suitable form as is well known in the art. For example, the drive mechanism 9 may include guideways for guiding the movement of the upper portion 5a relative to the bottom portion 5b, a linear motor that provides the motive force to move the upper portion 5a, and a linear encoder that provides position feedback so the upper portion 5a may be positioned accurately relative to the bottom portion 5b. It should be understood that the although in this embodiment the upper portion is moved relative to the bottom portion 5b, the bottom portion 5b may be moved relative to the upper portion 5a. Additionally, the tool body 5 may have more than two portions, e.g., the tool 10 may include an intermediate portion between the upper and lower portions, and the various portions may be moved relative to each other in any suitable way. Moreover, the tool 5 need not have movable portions like that shown, and instead the needles 4 may be actuated using other mechanisms.

Figure 3:
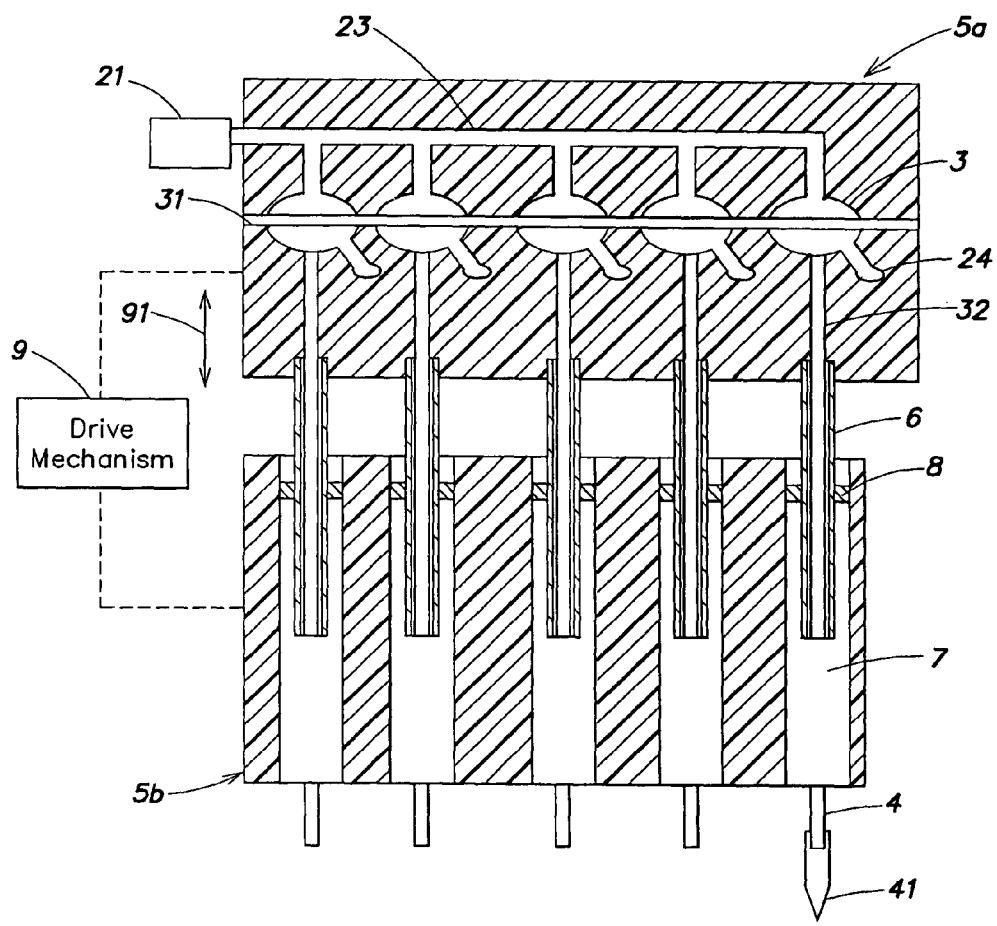
FIG. 3 is a cross-sectional view of the tool in FIG. 2.

FIG. 3 shows a schematic cross-sectional view of the tool 10 shown in FIG. 2. In this illustrative embodiment, the plungers 6 are secured at a top end to the upper portion 5a of the tool body 5 and move up and down in the direction shown by arrow 91 when the upper portion 5a is driven by the drive mechanism 9. This causes the plungers 6 to move relative to the lower portion 5b in a corresponding channel 7, e.g., a cylindrical bore in the lower portion 5b. One or more seals 8, such as an elastomeric member, resist fluid flow from within the channel 7 past the plunger 6. The seal(s) 8 may be stationary relative to the channel 7, or move with the plunger in the channel wall. The seal created may be enhanced by the use of a suitable lubricant or other material on the plunger 6. Movement of the plungers 6 in their respective channels 7 can create a suction/pressure at a corresponding needle 4, e.g., so a liquid can be aspirated or dispensed, as is well known in the art. The needles 4 may carry a replaceable pipette tip 41 as is known in the art.

Figure 4:
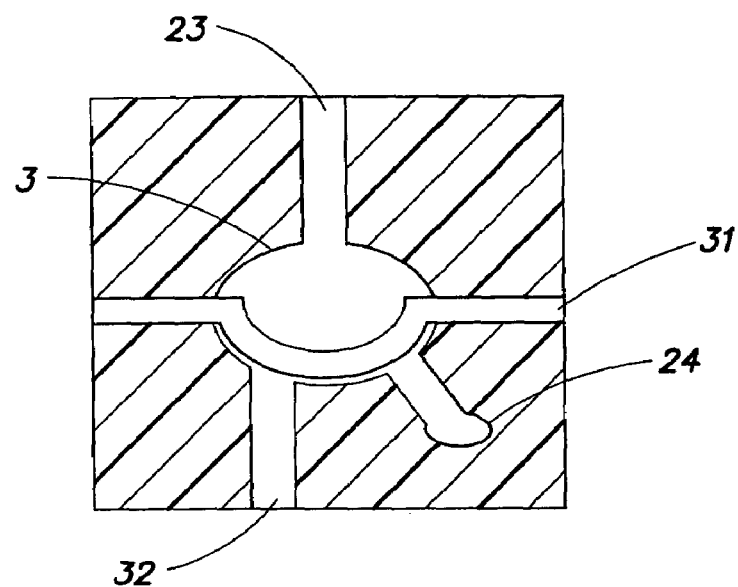
FIG. 4 is a schematic view of a valve that controls actuation of a corresponding needle in a closed state.
Figure 5:
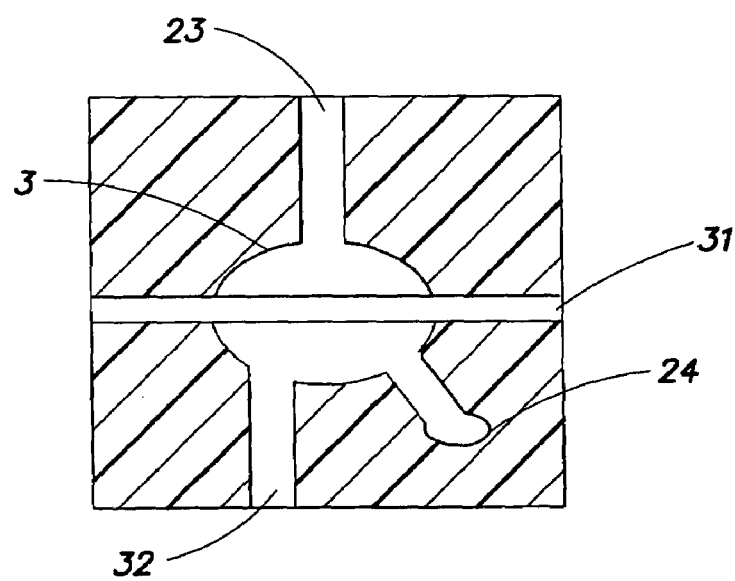
FIG. 5 is a schematic view of the FIG. 6 valve in an open state.

In this embodiment, the plungers 6 are porous, e.g., the plungers 6 have a hole or passageway that extends through the length of the plungers 6. The passageway allows fluid (gas or liquid) to pass through the plunger 6. The passageways for each plunger 6 communicate with an actuator 3, e.g., a membrane valve as shown in FIG. 3, via a line 32. The actuators 3 may open or close the passageways by operation of the membrane valve. For example, as shown in FIG. 4, when a suitable control signal, e.g., fluid pressure, is supplied on a line 23 to the actuators 3, the flexible member 31 may deform and prevent communication between the line 32 and a line 24. Alternately, as shown in FIG. 5, when the fluid pressure is released and/or a vacuum is applied, the flexible member 31 may retract, allowing communication between the line 32 and the line 24. As a result, the passageways may be opened or closed by the valves. A closed passageway allows a plunger 6 to create a suction/pressure in the channel 7 when the plunger 6 moves. However, an open passageway may prevent a suction/pressure from being created by movement of the plunger 6 since fluid may be supplied from the line 24 to the plunger passageway. That is, the line 24 may be open to ambient air pressure or supplied with a fluid at a suitable pressure to prevent movement of the plunger from causing the needle to aspirate/dispense a sample.

Control of the action at the needles 4 may be further controlled by controlling the fluid in the line 24. For example, the line 24 may be open to ambient air pressure so that opening and closing of the actuators 3 effectively closes or opens the passageway. Alternately, fluid may be supplied under pressure to the line 24, e.g., so that a liquid or gas may be selectively supplied through an open valve, through the plunger 6 and expelled from the corresponding needle. A vacuum may also be applied to the lines 24 so that when a passageway is opened by an actuator 3, fluid may be aspirated by a selected needle without requiring movement of plungers 6. Thus, aspirating/dispensing samples from needles 4 may be controlled by controlling fluid flow through the passageways independent of, or in conjunction with, movement of the plungers 6. Switching of fluid flow to the lines 23 and 24 may be controlled by the switches 21 and 22, respectively. The switches 21 and 22 may be electrically operated valves that switch the lines 23 and 24 between one or more fluid supply lines, e.g., lines that provide a vacuum, fluid under pressure or ambient air pressure.

As should be appreciated by those of skill in the art, the membrane valves shown are only one way that an actuator 3 for controlling the passageways may be implemented. The actuators 3 may include two or more membrane valves in a cascaded arrangement to allow truly individual control of the passageways, and of course other types of valves or other devices may be used to open or close the passageways. Of course, individually controlled valves could be used to open or close each passageway rather than using the matrix type valve arrangement shown.

Figure 6:
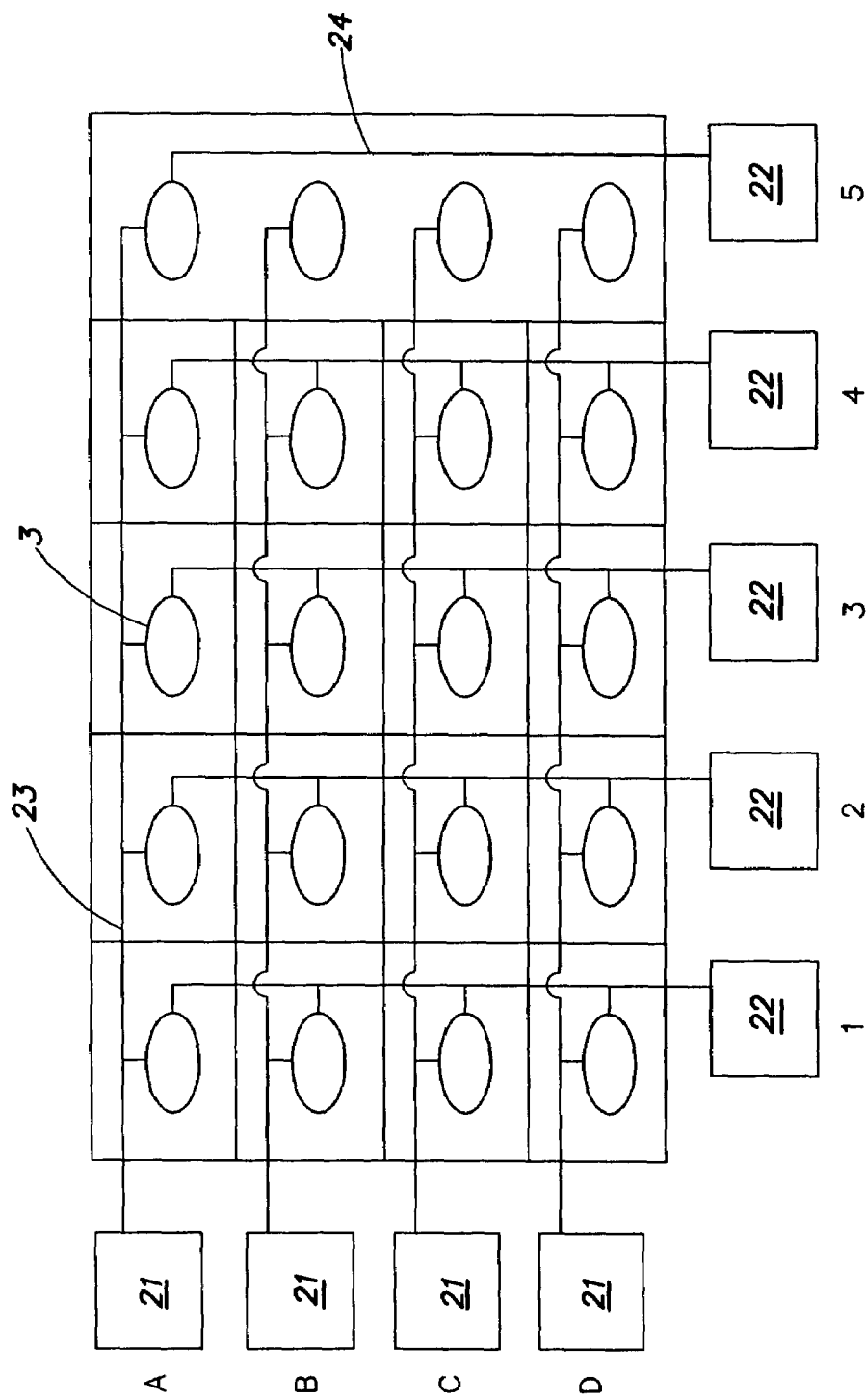
FIG. 6 is a plan view of the tool shown in FIG. 2 and illustrates how individual needle actuators may be addressed.

FIG. 6 shows a schematic plan view of the upper portion 5a of the tool 10. In this schematic view, the lines 23 provide control signals to rows A-D of actuators 3 via a corresponding switch 21. Drive signals are provided to columns 1-5 of actuators 3 via a corresponding switch 22. Thus, in this illustrative embodiment, each control switch 21 provides a control signal approximately simultaneously to all actuators 3 in the corresponding row via a control line 23. The control signal provided to a row of actuators 3 may cause the actuators 3 to change state between an open and closed state. Similarly, each of the drive switches 22 may approximately simultaneously provide a drive signal to all actuators 3 in a corresponding column along a drive line 24. Accordingly, individual passageways may be addressed, e.g., opened or closed, by providing a control signal along the actuator's corresponding control line 23, and a drive signal along the actuator's corresponding drive line 24 may control the actuation of the needle. For example, the passageway corresponding to the actuator 3 in the top right corner of the tool 10 as shown in FIG. 3 (position A-5) may be opened by providing a control signal from the control switch 21 for row A suitable to open the valve and allow flow through the passageway. Flow through the passageway may be controlled by controlling flow through the lines 24. That is, even if the valve for the passageway at position A-5 is opened, if flow is not allowed in the line 24 for that valve, e.g., the switch 22 for column 5 prevents flow in the line 24, fluid will not flow in the passageway. Thus, flow for the passageway may be controlled by controlling flow in the lines 24 as well. As a result, individual needles 4 may be actuated by providing appropriate signals to the lines 23 and 24, e.g., rows and/or columns, of actuators in the tool 10.

It should also be appreciated that selected groups of actuators 3 may be addressed by providing appropriate signals along the rows A-D and columns 1-5. For example, all needles on the tool 10, or selected needles, in a particular row or column may be approximately simultaneously actuated in a similar way, e.g., all of the actuators 3 in row A may aspirate a liquid by providing an appropriate control signal from the control switch 21 for row A to close the valves in the row A, providing appropriate control signals from the switches 21 for rows B-D to open the valves in rows B-D, and providing appropriate drive signals from the drive switches 22 for columns 1-5 to allow flow through the lines 24 while the plungers 6 are moved upwardly by the drive mechanism 9. Such a set of control signals may allow only the needles in row A to aspirate/dispense a sample. It will be appreciated that other selected groups of needles may be approximately simultaneously actuated by providing signals on appropriate control and drive lines 23 and 24 and/or moving the plungers 6 appropriately by the drive mechanism 9.

The plungers 6 and upper and lower portions 5a and 5b may be made of any suitable material(s), such as plastic, glass or suitable metal, and the channels, lines, chambers and other features may be formed in any suitable way using any suitable process. For example, the upper and lower portions 5a and 5b may be made of multiple layers of plastic material that have grooves, channels or are otherwise formed to create the desired lines, channels, etc. in the tool body 10. These layers may be joined together, e.g., by heating the layers and pressing them together, to form a unitary block. The membrane valves 31 may be formed by positioning a flexible member 6, such as a sheet of silicone rubber, between the layers of the upper portion 5a and securing the layers. The construction of membrane valves is well known, and alternate methods of construction will be appreciated by those of skill in the art.

The control and drive signals may also cause the membrane valves to perform other actuation operations with respect to the needles, such as pumping fluid through a corresponding needle and/or drawing or expelling a metered amount of fluid into or out of a corresponding needle 4. Pumping and metering operations may be performed by, for example, moving the flexible member in a valve to a closed state, closing a drive line 24 for the valve at a drive switch 22, and moving the flexible member in the valve to an open state, thereby causing fluid to be drawn into the needle 4. Movement of the flexible member may be closely controlled to perform accurate fluid metering through the valve's needle, e.g., by controlling the amount of fluid drawn from the valve by the control line 23. Such control can be performed by a metering piston coupled to the control line 23 or drive line 24, by accurately timing the opening and closing of a valve in the control switch 21 while supplying a constant fluid flow through the valve, or other means as will be appreciated by those of skill in the art.

It should be appreciated that although the control and drive switches in this illustrative embodiment control fluid flow to corresponding rows and columns of valves, the switches may provide other signal types to the actuators, such as electrical, optical, magnetic and other signal types. Similarly, the actuators and/or valves in this embodiment may include or be replaced with any other suitable element(s), such as electrical or optical relays, transistors, optical valves, etc., and the actuators 3 may include other drive elements, such as hydraulic rams, solenoid actuators, motors, and so on. Therefore, any suitable arrangement of elements may be used as actuators to receive control and drive signals and actuate a corresponding needle.

While the invention has been described with reference to various illustrative embodiments, the invention is not limited to the embodiments described. Thus, it is evident that many alternatives, modifications, and variations of the embodiments described will be apparent to those skilled in the art. For example, the porosity of the passageways in the plungers may be arranged to operate as a filter for fluid supplied to or drawn from a needle. Accordingly, embodiments of the invention as set forth herein are intended to be illustrative, not limiting. Various changes may be made without departing from the invention.

The invention claimed is:

1. A material handling tool, comprising:
   a tool body;
   a plurality of needles mounted to the tool body, each of the plurality of needles constructed and arranged to remove material from a work area and deposit material on a work area;
   a plurality of plungers moveable in the tool body, each of the plurality of plungers associated with a corresponding one of the plurality of needles, wherein each of the plungers has a passageway that allows fluid flow through the plunger; and
   a controller constructed and arranged to individually address each of the passageways so that flow in each of the passageways is individually controlled, wherein the controller comprises a plurality of actuators, each of the actuators including a membrane valve that controls fluid flow with respect to a corresponding passageway and is capable of opening and closing a corresponding passageway, and a plurality of drive switches that controls flow through a passageway opened by an actuator.

2. The tool of claim 1, wherein the controller comprises a plurality of control switches that provides signals to the plurality of actuators to open and close a corresponding passageway.

3. The tool of claim 2, wherein each of the plurality of control switches comprises a valve that provides a fluid signal to a corresponding actuator.

4. The tool of claim 1, wherein each of the plurality of drive switches includes a valve that provides a fluid flow for a corresponding passageway.

5. The tool of claim 1, wherein closing of a passageway of a plunger results in one of drawing fluid into or expelling fluid from a corresponding needle when the plunger is moved in the tool body.

6. The tool of claim 1, wherein one portion of each plunger is secured to a first portion of the tool body and a second portion of each plunger is slidably engaged with a channel in a second portion of the tool body such that movement of the first portion of the tool body relative to the second portion of the tool body causes a pressure change in each channel for plungers that have their passageway closed.

7. A material handling tool, comprising:
   a tool body;
   a plurality of needles mounted to the tool body, each of the plurality of needles constructed and arranged to remove material from a work area and deposit material on a work area;
   a plurality of plungers moveable in the tool body, each of the plurality of plungers associated with a corresponding one of the plurality of needles, wherein each of the plungers has a passageway that allows fluid flow through the plunger; and
   a first number of membrane valves, each membrane valve associated with a corresponding plunger and controlling flow for the passageway in the plunger; and
   a valve controller constructed and arranged to control each of the membrane valves by providing signals to the membrane valves;
   wherein the valve controller is adapted to control the membrane valves to individually control flow for each passageway.

8. The tool of claim 7, wherein the valve controller includes a plurality of first valves that each provide an air pressure signal to a corresponding group of membrane valves to control the membrane valves between open and closed states to open and close a corresponding passageway.

9. The tool of claim 8, wherein the valve controller includes a plurality of second valves that each provide a fluid flow to corresponding membrane valves.

10. The tool of claim 7, wherein the plurality of needles and corresponding membrane valves are arranged in an M×N array.

11. The tool of claim 10, wherein the valve controller includes M valves that each provide an air pressure signal to membrane valves in a corresponding row.

12. The tool of claim 10, wherein the valve controller includes N valves that each provide a fluid flow to membrane valves in a corresponding column.

13. The tool of claim 10, wherein closing of a passageway of a plunger results in one of drawing fluid into and expelling fluid from a corresponding needle when the plunger is moved in the tool body.

14. The tool of claim 10, wherein the valve controller is mounted to the tool body.

15. The tool of claim 7, wherein the valve controller is adapted to control the membrane valves to simultaneously control flow for a plurality of passageways.

* * * * *